United States Patent [19]

Mattioli et al.

[11] 4,142,402
[45] Mar. 6, 1979

[54] DEPOSITION TEST COUPON

[75] Inventors: Terrence W. Mattioli, King of Prussia; John R. Schieber, Holland, both of Pa.

[73] Assignee: Betz Laboratories, Inc., Trevose, Pa.

[21] Appl. No.: 883,769

[22] Filed: Mar. 6, 1978

[51] Int. Cl.² .................................................. G01N 17/00
[52] U.S. Cl. ........................................ 73/61.2; 422/53
[58] Field of Search ................... 73/61.2, 64.4, 86; 23/230 C, 253 C

[56] References Cited

U.S. PATENT DOCUMENTS

| 2,351,644 | 6/1944 | Talley et al. ................... 23/253 C |
| 2,710,539 | 6/1955 | Pollack ............................ 73/64.4 |
| 3,116,117 | 12/1963 | Marsh et al. ................... 23/253 C |

FOREIGN PATENT DOCUMENTS 466653  5/1927  Fed. Rep. of Germany ............ 73/64.4

Primary Examiner—Richard C. Queisser
Assistant Examiner—Joseph W. Roskos
Attorney, Agent, or Firm—Alexander D. Ricci; Steven H. Markowitz

[57] ABSTRACT

A test coupon, more particularly a deposition test coupon, for measuring the deposition rate of scale on surfaces in contact with a scale-forming medium such as industrial cooling water.

14 Claims, 3 Drawing Figures

DEPOSITION TEST COUPON

As is well known in the art, industrial process streams contain ingredients, either naturally occurring, as contaminants, or formed by the combination of anions and cations or mixtures thereof, which can and often do cause deposition problems.

For example, depending on the water source and process conditions, industrial water can contain alkaline earth metal or transition metal cations such as calcium, barium, magnesium, iron, etc; and such anions as carbonate, phosphate, sulphate, oxalate, silicate, etc. The combination of these anions and cations could, accordingly, form such potential depositing salts as calcium carbonate, calcium sulphate, calcium phosphate, magnesium carbonate, magnesium sulphate, etc. When the concentration of any such salts which are formed exceeds their solubility limit, they precipitate out of the water in the form of scale. The concentration of these scale-forming salts can increase as a result of partial water evaporation, or changes in pH, temperature or pressure of the water. The amount of scale formation generally depends on pH, temperature and type of salt formed. The scale thus formed will deposit on surfaces in contact with the aqueous medium, such as flow pipes, storage tanks, heat exchanger surfaces, etc. These deposits can prevent effective heat transfer, interfere with fluid flow through pipes, facilitate corrosion, and harbor bacteria.

Also, for example, the refinement of petroleum hydrocarbon is accomplished by the thermal or catalytic cracking of heavier petroleum hydrocarbon feed stocks such as light or heavy gas oils, cycle stocks, virgin or topped crude oils, etc. All known cracking processes involve the heating of the feed to a high temperature and the passage thereof through heated tubes, reactors, convectors, and tower stills, resulting in the formation of scale within the petroleum hydrocarbon. These scales deposit on the surfaces in contact with the heated petroleum hydrocarbon, reducing the bores of conduits and vessels to impede flow therethrough, impairing thermal transfer and clogging filter screens, valves and traps. The formation of such deposits necessitates frequent equipment shut-downs for tedious and costly cleaning operations which can result in increased processing cycles and a large proportion of "down-time" during which the process is not functioning.

Of course, deposition problems are not limited to liquid mediums. For example, such problems exist in the cold end of industrial boiler systems, that is, the parts of the boiler system through which combustion gases flow after performing their primary purpose of heating water, producing steam, and/or superheating steam. These combustion gases, which typically contain combustion products in the form of deposit-forming particles, will flow, in larger boiler systems, through an economizer, an air heater, collection equipment and then through the exhaust stack. Accordingly, these deposit-forming particles are potential problems since they will deposit on the cold end equipment surfaces which are exposed to the combustion gases.

While many effective treatments have been developed to help alleviate such deposition-related problems, there has always existed the need for testing equipment and methods to both define the nature and extent of the deposition problem and to evaluate the effectiveness of the treatment.

Initially, such tests took the form or simply inspecting surfaces of fouled equipment. This test is undesirable since the equipment can be irreparably damaged by the time the inspection takes place. Furthermore, such inspections often can only take place during "downtime", resulting in severe time limitations with respect to when the equipment or treatment can be evaluated.

Needless to say, this inspection test has been improved upon considerably and in various ways. The one general advantage of the improved tests over the inspection method relates to the elimination of the need to run the tests during process "down-time". Using the improved equipment and methods, the deposition problem can be defined and treatments can be evaluated "onstream", that is, while the process is in operation.

One such improved test method relates to the use of a common weight loss-type corrosion coupon which typically takes the form of a flat, rectangular piece of stock material such as low carbon steel. According to this method, the test coupon is merely inserted into a scale-forming medium in such a manner that there is relative movement between the medium and the coupon; and is allowed to collect deposits over a period of time. After a period of time elapses which is sufficient to ensure that a relatively uniform film of measurable thickness has formed on the coupon, it is removed and the film thickness is measured using a micrometer caliper. By comparing the measured thickness with the thickness of the clean coupon, it can be seen that the deposition problem and treatment effectiveness can be quantified. It can also seen that this method is rather time consuming insofar as the coupon must remain in the fluid long enough to ensure a film of both relatively uniform and measureable thickness. Furthermore, it is considered to be desirable to be able to utilize the deposition test coupon without the need for the micrometer.

The use of the micrometer has been eliminated to some extent by the development of a deposition test coupon having several equal sized holes therein (hereafter referred to as the perforated coupon). Utilizing the perforated coupon, deposition is considered to be indicated when the holes become covered. Thus, it can be seen that the quantitative deposition test coupon method using the micrometer to measure film thickness has been converted to some extent to a qualitative test. However, the perforated coupon has always been considered to have many inherent drawbacks. For example, if the rate of deposition is not great enough to cover the holes, the coupon can indicate that no deposition is occurring even though in reality deposits are forming on system surfaces. Also, even though the perforated coupon can indicate a deposition problem, provided it is severe enough to cover the holes, it has no capability of indicating the relative severity of the problem, that is, of qualitatively ranking the deposition rate. Put yet another way, this coupon is relatively insensitive to differences in deposition rates. Furthermore, the only way the perforated coupon test results can be verified is to run another test with another coupon.

According to the present invention, a deposition test coupon is provided which is qualitative in that it accommodates the elimination of quantitative measurements such as those which utilize the micrometer. Also, a deposition test coupon is provided which is capable of indicating problems at small deposition rates and which is relatively sensitive to different deposition rates in the test system so that treatment effectiveness is readily indicated. According to another feature of a deposition test coupon made according to the present invention, both the measurement of deposition rate and verification of the measurement are obtained in one step. Yet further, a deposition coupon made according to the present invention is relatively simple and inexpensive to make and use.

According to the present invention, a deposition test coupon is provided which contains openings of different cross-sectional areas (variable-sized). Accordingly, as deposition rates in the test medium (medium to be evaluated) increase, more openings will be covered-over by film deposits. Also, as treatment is added to the scale-forming medium and deposition rates accordingly decrease, less openings will be covered-over by film deposits. To facilitate ease of ranking of varying deposition rates, the openings should be mutually aligned to successively graduate in size. To verify the results of the deposition rate measurements obtained utilizing the subject test coupon, a first series of the openings take the form of holes in the coupon and a second series thereof take the form of notches in a first edge thereof. This verification feature is further refined by graduating the hole sizes in a first direction along the coupon and graduating the notch sizes in a direction therealong which is opposite the first direction. To even further refine this verification feature of the present invention, a second series of graduated notches are provided in the edge of the coupon which is opposite the first edge of which are provided the first series of notches. This second series of notches are graduated in size in a direction which is opposite the direction of graduation of the first series of notches.

These and other objects, features, and advantages of the present invention will become apparent from the following detailed description when taken in conjunction with the accompanying drawings, wherein like reference numerals refer to like parts, and in which.

Figure 1:
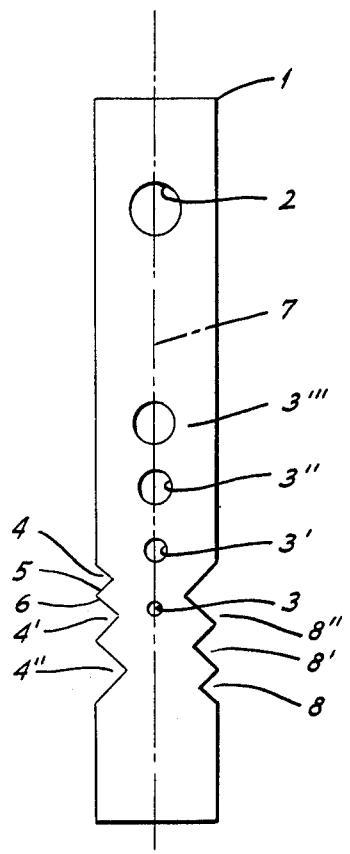
FIG. 1 is a plan view of a preferred embodiment according to the present invention.
Figure 2:
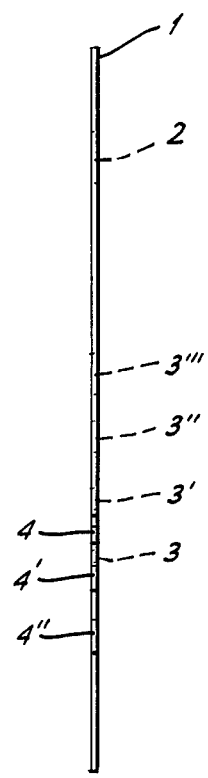
FIG. 2 is a side view of the embodiment illustrated in FIG. 1.

With reference now to the drawings, and particularly FIG. 1, reference numeral 1 generally refers to a deposition test coupon which is shown as a flat, rectangular piece of stock material. This shape is preferred due to its ease of manufacture and storage and ready adaptability into a process system to be tested (test system); however, it should be understood that the coupon could assume many other shapes as desired. For example, the test coupon could be a small cylindrical pipe which is coaxially aligned with and surrounded by a transparent outer pipe. This arrangement could then, for example, be arranged in a test system by-pass stream, and the fouling test coupon could be observed through the outer transparent pipe. Also for example, the coupon could be flat and circular or flat and square.

As already noted, test coupon 1 is to be used for measuring the deposition rate of scale on surfaces in contact with a scale-forming medium, such as an aqueous medium. The methods for inserting the subject coupon into a process stream are the same as those for standard corrosion coupons, which latter methods are indeed well known in the art. For example, the coupon could be supported in a test stream by a retractable test specimen assembly such as the one disclosed in U.S. Pat. No. 3,174,332. Also for example, the coupon could be supported in the stream by some form of strand attached to one end thereof. Reference numeral 2 in the drawing refers to a hole provided in the coupon to accommodate attachment thereof to the coupon support, be it a retractable or a strand support.

Shown in the coupon 1 are a first series of openings 3, 3', 3", and 3''' and a second series thereof 4, 4', and 4". As shown in FIG. 1, each series includes variable-sized openings, that is, the openings in each series have mutually different cross-sectional areas. By providing such a series of variable-sized openings, it is observed that the number of openings covered-over by scale will depend on the deposition rate of the scale, that is, as the deposition rate increases, more openings will plug. Accordingly, it can be seen that different deposition rates can be ranked by using a deposition test coupon with variable sized openings. For example, a deposition rate which covers openings 3, 3' and 3" would be considered to be higher than one which covers only opening 3. Openings 3-3''' are shown as spaced holes in that they are openings which each have a continuous border of coupon material, while openings 4-4" are shown as notches in that they are openings which each have a discontinuous border. While the notches could be spaced apart along the edge of the coupon, it is preferred that they be arranged as a continuous series of notches by joining the end 5 of one notch to the beginning 6 of another.

To accommodate ease of measurement, it is preferred that the openings in each series are mutually aligned to successively graduate in size. This is illustrated in FIG. 1 wherein holes 3-3''' are aligned along line 7 so that in moving from one hole to another from 3-3''' in this series, the cross-sectional areas constantly increase in size. Similarly, in moving from notch 4 to notch 4", the areas increase in size.

As shown in FIG. 1, the holes 3-3''' are arranged as a first series of variable-sized openings which are mutually aligned so as to successively increase in size in a first direction, that is in the present instance, from the bottom of the coupon to the top thereof. On the other hand, notches 4-4" are arranged as a second series of variable-sized openings which are mutually aligned so as to successively increase in a direction which is opposite the first direction (in which the holes increase in size). By providing such oppositely graduated openings, a double-check system is built into a single test coupon for determining the reproducibility of the results obtained. For example, if holes 3-3''' all are covered in a given test while none of the notches are covered, there is an indication that the test might not be valid (not reproducible), thus calling for rerunning the test. However, if, for example, holes 3-3" and notches 4 and 4' are all covered, the test results would appear to be valid so that no additional test(s) need be conducted. Taking this double-check idea further, it is preferred that a second series of notches 8, 8' and 8" be provided along another edge of coupon 1 to serve as a double-check system for notches 4-4". As shown in FIG. 1, notches 8-8" are arranged opposite to and have an opposite direction of size graduation with respect to notches 4-4".

Figure 3:
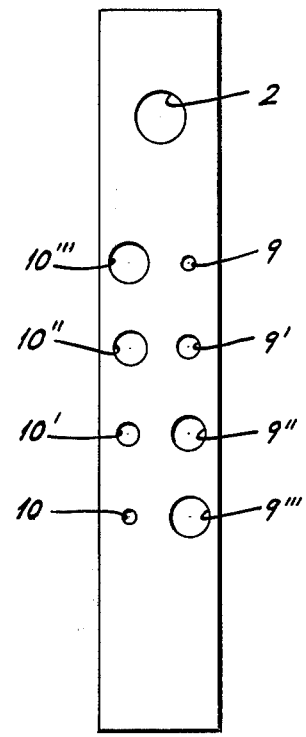
FIG. 3 is a modified embodiment according to the present invention in which two sets of holes are provided in the main body of a test coupon.

Illustrated in FIG. 3 is a modified embodiment of a deposition test coupon in accordance with the present invention wherein a modified double-check system is shown. Instead of using oppositely graduated series of holes and notches to determine the reproducibility of test results as shown in FIG. 1, according to this modified embodiment plural series of oppositely graduated holes 9–9''' and 10–10''' are used. Of course, additional double-check systems could be provided in the FIG. 3 embodiment by notching one or both edges of the coupon.

Having the benefit of the foregoing description of the present invention, it should now occur to the artisan that the specific construction of a deposition test coupon made according to the present invention could vary depending on the nature of the test system and the test methods to be used. For example, if the coupon is to be arranged in a flow pipe of the test system in fixed perpendicular relationship to the direction of fluid flow through the pipe, the notches should be bunched together along the edge of the coupon. Since it is known that the fluid flow profile through a pipe changes rather dramatically as the distance from the inside wall of the pipe increases, it is preferable to assure that the notches are all exposed to substantially the same flow profile. This type of problem might arise if a retractable test specimen assembly is used to support the coupon in the test medium. On the other hand, if the deposition test coupon is to be arranged in parallel relationship to the direction of fluid flow through the pipe, the notches can be either spaced apart or bunched since they will be subjected to substantially the same flow profile. This parallel arrangement would typically be experienced when the coupons are supported by flexible string. Also for example, if the process surfaces which are experiencing deposition problems do not corrode, the test coupon should also not corrode, e.g., stainless steel, polyvinyl chloride, etc. On the other hand, if it is suspected that corrosion is contributing to the deposition problem in the process system, the coupon should corrode in the medium as, for example, a coupon of low carbon steel will corrode in water.

EXAMPLES

A coupon as shown in FIG. 1 was tested in simulated cooling water to demonstrate the use of the subject deposition test coupon. The tests were conducted using a standard spinner technique as described in U.S. Pat. No. 3,960,576, and the coupon was low carbon steel. In accordance with that technique, the test coupons were suspended and rotated in a water bath for a given period of time. The water in the bath, of course, was the simulated cooling water. After the coupons were rotated in this environment for a predetermined time, 4 days, they were removed and visually inspected. The test conditions were as follows:

| | |
|---|---|
| Calcium ion concentration as $CaCO_3$ | 170 ppm |
| Magnesium ion concentration as $CaCO_3$ | 110 ppm |
| Silicon dioxide as $SiO_2$ | 15 ppm |
| Orthophosphate as $O-PO_4$ | 20 ppm |
| pH | 7 |
| Temperature | 120° F |
| Water Velocity | 1.3 fps |
| Test Duration | 4 days |

After four days of testing, which is considered to be a relatively short test period, the smallest hole was plugged and the second hole was about half-plugged. It was accordingly concluded that with the passage of time more holes would have plugged as expected.

Similarly, a deposition test coupon as shown in FIG. 1 was tested in a pilot plant gas scrubber through which was circulated a 15% aqueous limestone slurry. The pH of the system was about 7.8 and the coupon was located in the recirculation tank of the scrubber. After but 6 hours of testing, the smallest hole of the coupon had indeed plugged.

A deposition coupon made in accordance with the present invention would typically be used as follows to provide a qualitative measure of the effectiveness of deposit control treatments in an industrial water system wherein process equipment is experiencing deposition problems. Using a retractable test specimen support assembly, the coupon is inserted directly into a process water flow line so as to expose the coupon to the process water. A spot in the flow line should be chosen where the flow velocity past the coupon will approximately correspond to the velocity in the process equipment where the deposits are occurring. The coupon should be left in the system until several openings have plugged and the time required should be recorded. Next, a treatment is selected and applied and a clean coupon is inserted into the system for the same length of time as was the first one. If, after this same length of time has elapsed the second coupon has less plugged openings than did the first, the treatment is effective.

Having thus described our invention we claim:

1. A deposition test coupon comprising:
   a flat rectangular coupon having holes therein from one longitudinal end thereof to the other, said holes being graduated in size, and
   notches in opposite longitudinal edges of the coupon near the end thereof having the smallest size hole, the notches along each edge defining notched-out areas of graduated size,
   wherein the notches along one edge of the coupon are oppositely graduated with respect to the notches along the other edge.

2. A deposition test coupon according to claim 1, wherein said holes are circular.

3. A deposition test coupon according to claim 2, wherein said notches are continuous.

4. A deposition test coupon according to claim 3 which is made of non-corroding material.

5. A deposition test coupon according to claim 4 which is made of stainless steel.

6. A deposition test coupon according to claim 3 which is made of low carbon steel.

7. In a deposition test coupon for measuring the deposition rate of scale on surfaces in contact with a scale-forming medium, the improvement comprising:
   a first series of variable-sized openings in said coupon, which openings are mutually aligned so as to successively increase in size in a first direction, and
   a second series of variable-sized openings in said coupon, which openings are mutually aligned so as to successively increase in size in a second direction, wherein said first series of openings comprises spaced holes and wherein said second series comprises notches in an edge of said coupon.

8. A deposition test coupon according to claim 7, wherein said second direction is opposite said first direction.

9. In a deposition test coupon for measuring the deposition rate of scale on surfaces in contact with a scale-forming medium, the improvement comprising:
   a first series of variable-sized openings in said coupon, which openings are mutually aligned so as to successively increase in size in a first direction, and
   a second series of variable-sized openings in said coupon, which openings are mutually aligned so as to successively increase in size in a second direction, wherein each of said series of openings comprises notches in an edge of said coupon.

10. A deposition test coupon according to claim 9, wherein said second direction is opposite said first direction.

11. In a deposition test coupon for measuring the deposition rate of scale on surfaces in contact with a scale-forming medium, the improvement comprising:
a first series of variable-sized openings in said coupon, which openings are mutually aligned to successively increase in size in a first direction, and
a second series of variable-sized openings in said coupon, which openings are mutually aligned to successively increase in size in a second direction, wherein each opening in one of said first and second series of openings is equal in size to a corresponding opening in the other series of openings so as to provide for verified deposition measurements.

12. A deposition test coupon according to claim 11, wherein each of said series of openings comprises holes in said coupon.

13. A deposition test coupon according to claim 11, wherein said second direction is opposite said first direction.

14. A deposition test coupon according to claim 11, wherein the number of openings in said first series of openings is equal to the number of openings in said second series thereof.

* * * * *